United States Patent [19]

Endo et al.

[11] Patent Number: 4,608,367

[45] Date of Patent: Aug. 26, 1986

[54] γ-PYRONE PHOSPHORIC ESTER DERIVATIVES AND INSECTICIDAL AND MITICIDAL COMPOSITIONS THEREOF

[75] Inventors: Yoshinori Endo, Naruto; Hisashi Takao, Tokushima, both of Japan

[73] Assignee: Otsuka Kagaku Kabushiki Kaisha, Osaka, Japan

[21] Appl. No.: 758,735

[22] Filed: Jul. 25, 1985

[30] Foreign Application Priority Data

Jul. 31, 1984 [JP] Japan ................... 59-162078

[51] Int. Cl.$^4$ ............ A01N 57/02; C07F 9/165; C07F 9/24; C07F 9/65
[52] U.S. Cl. .................... 514/89; 514/90; 514/99; 544/157; 546/21; 549/222
[58] Field of Search .......... 544/157; 546/21; 549/222; 514/89, 90, 99

[56] References Cited

U.S. PATENT DOCUMENTS 2,905,700 9/1959 Metivier .................. 549/222
3,714,350 1/1973 Gough .................... 424/203

FOREIGN PATENT DOCUMENTS 92293 7/1981 Japan .

Primary Examiner—Richard L. Raymond
Attorney, Agent, or Firm—Murray and Whisenhunt

[57] ABSTRACT

γ-Pyrone phosphoric ester derivative represented by the general formula below is useful as an effective component of an insecticidal or miticidal composition for agricultural and horticultural uses.

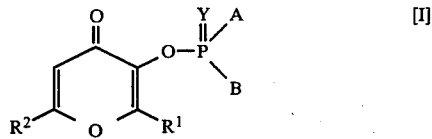

wherein $R^1$ is hydrogen, lower alkyl group, lower alkenyl group, cycloalkyl group or phenyl group, $R^2$ is hydrogen or lower alkyl group unsubstituted or substituted with halogen atom, A is —$SR^3$ or —$NR^4R^5$, B is $OR^6$, $R^3$ being lower alkyl group, cycloalkyl group or phenyl group, $R^4$ being hydrogen or lower alkyl group, $R^5$ being lower alkyl group, lower alkenyl group, cycloalkyl group, phenyl group or benzyl group, $R^4$ and $R^5$ may link to form piperidino or morpholino group, $R^6$ being lower alkyl group, cycloalkyl group or phenyl group, Y is oxygen or sulfur atom.

5 Claims, No Drawings

γ-PYRONE PHOSPHORIC ESTER DERIVATIVES AND INSECTICIDAL AND MITICIDAL COMPOSITIONS THEREOF

The present invention relates to γ-pyrone phosphoric ester derivative and insecticidal or miticidal composition containing the derivative as an effective component for agricultural and horticultural uses.

The present γ-pyrone phosphoric ester derivative is a novel compound which is not disclosed in literatures and is represented by the general formula [I] below.

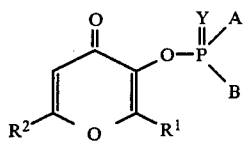

[I]

wherein $R^1$ is hydrogen, lower alkyl group, lower alkenyl group, cycloalkyl group or phenyl group, $R^2$ is hydrogen or lower alkyl group unsubstituted or substituted with halogen atom, A is $-SR^3$ or $-NR^4R^5$, B is $OR^6$, $R^3$ being lower alkyl group, cycloalkyl group or phenyl group, $R^4$ being hydrogen or lower alkyl group, $R^5$ being lower alkyl group, lower alkenyl group, cycloalkyl group, phenyl group or benzyl group, $R^4$ and $R^5$ may link to form piperidino or morpholino group, $R^6$ being lower alkyl group, cycloalkyl group or phenyl group, Y is oxygen or sulfur atom.

The present compound of the general formula [I] is very excellent in insecticidal and miticidal activities. Particularly, the present compound has a low toxicity to a warm-blooded animal and has excellent properties for developing further agricultural chemicals.

In the above general formula [I], examples of useful lower alkyl groups are straight-chain or branched-chain alkyl groups having 1 to 6 carbon atoms such as methyl, ethyl, propyl, isopropyl, butyl, tert-butyl, pentyl, hexyl, etc. Examples of useful cycloalkyl groups are those having 3 to 8 carbon atoms such as cyclopropyl, cyclobutyl, cyclopentyl, cyclohexyl, cycloheptyl, cyclooctyl, etc. Examples of lower alkenyl groups are straight-chain or branched-chain alkenyl groups having 2 to 6 carbon atoms such as vinyl, allyl, 2-butenyl, 3-butenyl, 1-methylallyl, 2-pentenyl, 2-hexenyl, etc. Examples of useful lower alkyl groups unsubstituted or substituted with halogen atom are fluoromethyl, chloromethyl, bromomethyl, 2-chloroethyl, 3-chloropropyl, 4-chlorobutyl, etc. in addition to the above enumerated lower alkyl groups.

The present compound can be prepared by various processes and preferably prepared by, for example, reacting 3-hydroxy-γ-pyrone derivative of the general formula

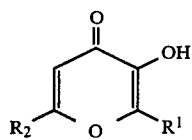

(II)

wherein $R^1$ and $R^2$ are same as above, with a phosphoric acid halide of the general formula

(III)

wherein A, B and Y are same as above, X is halogen atom.

3-Hydroxy-γ-pyrone derivative of the general formula [II] is a known compound and prepared, for example, according to Tetrahedron Lett., 1363 (1976), etc. Examples thereof are 3-hydroxy-γ-pyrone, 2-methyl-3-hydroxy-γ-pyrone, 2-ethyl-3-hydroxy-γ-pyrone, 2-isopropyl-3-hydroxy-γ-pyrone, 2-n-butyl-3-hydroxy-γ-pyrone, 2-isobutyl-3-hydroxy-γ-pyrone, 2-n-amyl-3-hydroxy-γ-pyrone, 2-n-hexyl-3-hydroxy-γ-pyrone, 2-cyclohexyl-3-hydroxy-γ-pyrone, 2-phenyl-3-hydroxy-γ-pyrone, 2-vinyl-3-hydroxy-γ-pyrone, 2-allyl-3-hydroxy-γ-pyrone, 2-hexenyl-3-hydroxy-γ-pyrone, 3-hydroxy-6-methyl-γ-pyrone, 3-hydroxy-6-chloromethyl-γ-pyrone, 3-hydroxy-6-bromomethyl-γ-pyrone, 2,6-dimethyl-3-hydroxy-γ-pyrone, 2-ethyl-3-hydroxy-6-methyl-γ-pyrone, 2-isopropyl-3-hydroxy-6-methyl-γ-pyrone, 2-isopropyl-3-hydroxy-6-chloromethyl-γ-pyrone, 2-isobutyl-3-hydroxy-6-methyl-γ-pyrone, 2-isobutyl-3-hydroxy-6-chloromethyl-γ-pyrone, 2-amyl-3-hydroxy-6-methyl-γ-pyrone, 2-cyclohexyl-3-hydroxy-6-methyl-γ-pyrone, 2-phenyl-3-hydroxy-6-methyl-γ-pyrone, 2-vinyl-3-hydroxy-6-methyl-γ-pyrone, etc.

Phosphoric acid halide to be reacted with the above pyrone derivative and represented by the general formula [III] is also a known compound and is inexpensively available industrially. Examples thereof are O,S-dimethylthiophosphoric acid chloride, O-methyl-S-ethylthiophosphoric acid chloride, O-methyl-S-n-propylthiophosphoric acid chloride, O-methyl-S-isopropylthiophosphoric acid chloride, O-methyl-S-n-butylthiophosphoric acid chloride, O-methyl-S-isobutylthiophosphoric acid chloride, O-methyl-S-sec-butylthiophosphoric acid chloride, O-methyl-S-cyclohexylthiophosphoric acid chloride, O-methyl-S-phenylthiophosphoric acid chloride, O-ethyl-S-methylthiophosphoric acid chloride, O,S-diethylthiophosphoric acid chloride, O-ethyl-S-isopropylthiophosphoric acid chloride, O-ethyl-S-n-butylthiophosphoric acid chloride, O-ethyl-S-cyclohexylthiophosphoric acid chloride, O-ethyl-S-phenylthiophosphoric acid chloride, O-n-propyl-S-methylthiophosphoric acid chloride, O-n-propyl-S-ethylthiophosphoric acid chloride, O-n-propyl-S-n-butylthiophosphoric acid chloride, O-n-propyl-S-cyclohexylthiophosphoric acid chloride, O-n-butyl-S-methylthiophosphoric acid chloride, O,S-dibutylthiophosphoric acid chloride, O,S-dimethyldithiophosphoric acid chloride, O,S-diethyldithiophosphoric acid chloride, O-methyl-S-ethyldithiophosphoric acid chloride, O-methyl-S-n-propyldithiophosphoric acid chloride, O-methyl-S-isopropyldithiophosphoric acid chloride, O-methyl-S-n-butyldithiophosphoric acid chloride, O-methyl-S-cyclohexyldithiophosphoric acid chloride, O-ethyl-S-n-propyldithiophosphoric acid chloride, O-n-butyl-S-ethyldithiophosphoric acid chloride, O-cyclohexyl-S-ethyldithiophosphoric acid chloride, O-methyl-N-methylamidophosphoryl chloride, O-methyl-N-ethylamidophosphoryl chloride, O-methyl-N-n-propylamidophosphoryl chloride, O-methyl-N-isopropylamidophosphoryl chloride, O-methyl-N-n-butylamidophosphoryl chloride, O-methyl-N-isobutylamidophosphoryl chloride, O-methyl-N-sec-butylamidophosphoryl chloride, O-methyl-N-cyclohexylamidophosphoryl chloride, O-methyl-N,N-dimethylamidophosphoryl chloride, O-methyl-N,N-diethylamidophosphoryl chloride, O-ethyl-N-methylamidophosphoryl chloride, O-ethyl-N-ethylamidophosphoryl chloride, O-ethyl-N-n-propylamidophosphoryl chloride, O-ethyl-N-iso-propylamidophosphoryl chloride, O-ethyl-N-n-butylamidophosphoryl chloride, O-ethyl-N-isobutylamidophosphoryl chloride, O-ethyl-N-cyclohexylamidophosphoryl chloride, O-propyl-N-ethylamidophosphoryl chloride, O-propyl-N-propylamidophosphoryl chloride, O-butyl-N-ethylamidophosphoryl chloride, O-methyl-N-methylamidothiophosphoryl chloride, O-methyl-N-ethylamidothiophosphoryl chloride, O-methyl-N-n-propylamidothiophosphoryl chloride, O-methyl-N-iso-propylamidothiophosphoryl chloride, O-methyl-N-n-butylamidothiophosphoryl chloride, O-methyl-N-isobutylamidothiophosphoryl chloride, O-methyl-N-sec-butylamidothiophosphoryl chloride, O-methyl-N-cyclohexylamidothiophosphoryl chloride, O-methyl-N,N-dimethylamidothiophosphoryl chloride, O-methyl-N,N-diethylamidothiophosphoryl chloride, O-ethyl-N-methylamidothiophosphoryl chloride, O-ethyl-N-ethylamidothiophosphoryl chloride, O-ethyl-N-n-propylamidothiophosphoryl chloride, O-ethyl-N-iso-propylamidothiophosphoryl chloride, O-ethyl-N-n-butylamidothiophosphoryl chloride, O-ethyl-N-isobutylamidothiophosphoryl chloride, O-ethyl-N-sec-butylamidothiophosphoryl chloride, O-ethyl-N-cyclohexylamidothiophosphoryl chloride, O-ethyl-N,N-diethylamidothiophosphoryl chloride, O-ethyl-N-phenylamidothiophosphoryl chloride, O-propyl-N-ethylamidothiophosphoryl chloride, O-butyl-N-ethylamidothiophosphoryl chloride, etc.

The preparation of the compound [I] by the reaction of the compound [II] and the compound [III] is preferably conducted in an appropriate solvent in the presence of an acid acceptor. Examples of solvents used in the reaction are dioxane, tetrahydrofuran, diethyl ether and like ethers; methylene chloride, chloroform, carbon tetrachloride and like halogenated hydrocarbons; benzene, toluene, xylene and like aromatic hydrocarbons; acetone, methyl ethyl ketone, methyl isobutyl ketone and like aliphatic ketones; acetonitrile, propionitrile and like aliphatic nitriles; dimethyl formamide, dimethyl acetoamide and like acid amides; dimethyl sulfoxide, sulfolan and like sulfoxides; etc. The acid acceptor includes a usual compound which reacts with the acid. Examples thereof are sodium hydroxide, potassium hydroxide and like alkali metal hydroxides; sodium carbonate, potassium carbonate, sodium bicarbonate, potassium bicarbonate and like alkali metal carbonate; sodium hydride; sodium methylate, sodium ethylate and like alcoholates; triethylamine, dimethylaniline, diethylaniline, pyridine and like aliphatic, aromatic and heterocyclic amines; etc. The acid acceptor is used usually in 0.5 to 3.0 moles, preferably 1.0 to 1.5 moles per mole of the starting material [II]. Further, this reaction can be conducted by reacting a salt, preferably sodium salt or potassium salt of the 3-hydroxy-γ-pyrone derivative and the phosphoric acid halide, in place of using the acid acceptor.

The reaction of the invention can be carried out in a wide range of temperature and generally conducted from −30° C. to boiling temperature of the solvent, preferably from 0° to 100° C. The reaction time depends on the starting materials but the reaction is usually completed within 1 to 5 hours. The present compound obtained as above can be easily isolated and purified by a usual means such as extraction with solvent, dilution with solvent, distillation, recrystallization, column chromatography, etc. to obtain the desired γ-pyrone phosphoric ester derivative of the general formula [I] in a high purity.

The followings are typical examples of the γ-pyrone phosphoric ester derivatives of the invention.

3-(O-methyl, S-methylthiophosphoryloxy)-γ-pyrone  Compound 1
3-(O-methyl, S-n-propylthiophosphoryloxy)-γ-pyrone  Compound 2
3-(O-methyl, S-isobutylthiophosphoryloxy)-γ-pyrone  Compound 3
3-(O-methyl, S-sec-butylthiophosphoryloxy)-γ-pyrone  Compound 4
3-(O-methyl, S-isopentylthiophosphoryloxy)-γ-pyrone  Compound 5
3-(O-ethyl, S-n-propylthiophosphoryloxy)-γ-pyrone  Compound 6
3-(O-ethyl, S-isopropylthiophosphoryloxy)-γ-pyrone  Compound 7
3-(O-ethyl, S-isobutylthiophosphoryloxy)-γ-pyrone  Compound 8
3-(O-n-propyl, S-n-propylthiophosphoryloxy)-γ-pyrone  Compound 9
3-(O-n-butyl, S-n-propylthiophosphoryloxy)-γ-pyrone  Compound 10
3-(O-n-hexyl, S-n-propylthiophosphoryloxy)-γ-pyrone  Compound 11
3-(O-isopropyl, S-n-propylthiophosphoryloxy)-γ-pyrone  Compound 12
3-(O-n-propyl, S-isobutylthiophosphoryloxy)-γ-pyrone  Compound 13
3-(O-isobutyl, S-isobutylthiophosphoryloxy)-γ-pyrone  Compound 14
3-(O-isobutyl, S-ethylthiophosphoryloxy)-γ-pyrone  Compound 15
3-(O-sec-butyl, S-n-propylthiophosphoryloxy)-γ-pyrone  Compound 16
3-(O-n-butyl, S-isobutylthiophosphoryloxy)-γ-pyrone  Compound 17
3-(O-sec-butyl, S-isobutylthiophosphoryloxy)-γ-pyrone  Compound 18
3-(O-isopropyl, S-isobutylthiophosphoryloxy)-γ-pyrone  Compound 19
3-(O-ethyl, S-ethylthiophosphoryloxy)-γ-pyrone  Compound 20
3-(O-ethyl, S-phenylthiophosphoryloxy)-γ-pyrone  Compound 21
3-(O-ethyl, S-cyclohexylthiophosphoryloxy)-γ-pyrone  Compound 22
3-(O-methyl, S-cyclohexylthiophosphoryloxy)-γ-pyrone  Compound 23
3-(O-cyclohexyl, S-isobutylthiophosphoryloxy)-γ-pyrone  Compound 24
3-(O-phenyl, S-isobutylthiophosphoryloxy)-γ-pyrone  Compound 25
6-chloromethyl-3-(O-ethyl, S-n-propylthiophosphoryloxy)-γ-pyrone  Compound 26
6-chloromethyl-3-(O-ethyl, S-isobutylthiophosphoryloxy)-γ-pyrone  Compound 27
6-methyl-3-(O-ethyl, S-n-propylthiophosphoryloxy)-γ-pyrone  Compound 28

6-methyl-3-(O-ethyl, S-isobutylthiophosphoryloxy)-γ-pyrone   Compound 29

6-methyl-3-(O-ethyl, S-isopentylthiophosphoryloxy)-γ-pyrone   Compound 30

6-methyl-3-(O-ethyl, S-isopropylthiophosphoryloxy)-γ-pyrone   Compound 31

2,6-dimethyl-3-(O-ethyl, S-n-propylthiophosphoryloxy)-γ-pyrone   Compound 32

6-methyl-3-(O-methyl, S-isobutylthiophosphoryloxy)-γ-pyrone   Compound 33

6-methyl-3-(O-methyl, S-n-propylthiophosphoryloxy)-γ-pyrone   Compound 34

3-(O-ethyl, S-n-propylthiophosphoryloxy)-2-methyl-γ-pyrone   Compound 35

3-(O-ethyl, S-n-propylthiophosphoryloxy)-2-ethyl-γ-pyrone   Compound 36

3-(O-ethyl, S-isobutylthiophosphoryloxy)-2-methyl-γ-pyrone   Compound 37

3-(O-ethyl, S-n-propylthiophosphoryloxy)-2-n-propyl-γ-pyrone   Compound 38

3-(O-methyl, S-n-propylthiophosphoryloxy)-2-isopropyl-γ-pyrone   Compound 39

3-(O-methyl, S-isobutylthiophosphoryloxy)-2-isopropyl-γ-pyrone   Compound 40

3-(O-methyl, S-sec-butylthiophosphoryloxy)-2-isopropyl-γ-pyrone   Compound 41

3-(O-ethyl, S-n-propylthiophosphoryloxy)-2-isopropyl-γ-pyrone   Compound 42

3-(O-ethyl, S-isobutylthiophosphoryloxy)-2-isopropyl-γ-pyrone   Compound 43

3-(O-ethyl, S-n-propylthiophosphoryloxy)-2-sec-butyl-γ-pyrone   Compound 44

3-(O-ethyl, S-isobutylthiophosphoryloxy)-2-sec-butyl-γ-pyrone   Compound 45

3-(O-ethyl, S-n-propylthiophosphoryloxy)-2-isobutyl-γ-pyrone   Compound 46

3-(O-ethyl, S-isobutylthiophosphoryloxy)-2-isobutyl-γ-pyrone   Compound 47

3-(O-methyl, S-isobutylthiophosphoryloxy)-2-n-hexyl-γ-pyrone   Compound 48

3-(O-methyl, S-isobutylthiophosphoryloxy)-2-isobutyl-γ-pyrone   Compound 49

3-(O-ethyl, S-n-propylthiophosphoryloxy)-2-cyclohexyl-γ-pyrone   Compound 50

3-(O-ethyl, S-isobutylthiophosphoryloxy)-2-cyclohexyl-γ-pyrone   Compound 51

3-(O-ethyl, S-n-propylthiophosphoryloxy)-2-cyclopropyl-γ-pyrone   Compound 52

3-(O-ethyl, S-n-propylthiophosphoryloxy)-2-phenyl-γ-pyrone   Compound 53

3-(O-ethyl, S-isobutylthiophosphoryloxy)-2-phenyl-γ-pyrone   Compound 54

3-(O-ethyl, S-n-propylthiophosphoryloxy)-2-allyl-γ-pyrone   Compound 55

3-(O-ethyl, S-n-propylthiophosphoryloxy)-2-methallyl-γ-pyron   Compound 56

3-(O-ethyl, S-n-propylthiophosphoryloxy)-2-propenyl-γ-pyrone   Compound 57

3-(O-ethyl, S-n-propyldithiophosphoryloxy)-γ-pyrone   Compound 58

3-(O-ethyl, S-isobutyldithiophosphoryloxy)-γ-pyrone   Compound 59

6-methyl-3-(O-ethyl, S-isobutyldithiophosphoryloxy)-γ-pyrone   Compound 60

3-(O-ethyl, S-n-propyldithiophosphoryloxy)-2-methyl-γ-pyrone   Compound 61

3-(O-ethyl, S-n-propyldithiophosphoryloxy)-2-isopropyl-γ-pyrone   Compound 62

3-(O-ethyl, S-isobutyldithiophosphoryloxy)-2-isopropyl-γ-pyrone   Compound 63

3-(O-methyl, S-isobutyldithiophosphoryloxy)-γ-pyrone   Compound 64

3-(O-methyl, S-n-propyldithiophosphoryloxy)-γ-pyrone   Compound 65

3-(O-methyl, S-n-propyldithiophosphoryloxy)-2-isopropyl-γ-pyrone   Compound 66

3-(O-methyl, S-sec-butyldithiophosphoryloxy)-γ-pyrone   Compound 67

3-(O-methyl, S-isobutyldithiophosphoryloxy)-2-isopropyl-γ-pyrone   Compound 68

3-(O-methyl, S-isobutyldithiophosphoryloxy)-2-sec-butyl-γ-pyrone   Compound 69

3-(O-methyl-N-methylamidophosphoryloxy)-γ-pyrone   Compound 70

3-(O-methyl-N-ethylamidophosphoryloxy)-γ-pyrone   Compound 71

3-(O-methyl-N-n-propylamidophosphoryloxy)-γ-pyrone   Compound 72

3-(O-methyl-N-isopropylamidophosphoryloxy)-γ-pyrone   Compound 73

3-(O-methyl-N-n-butylamidophosphoryloxy)-γ-pyrone   Compound 74

3-(O-methyl-N-isobutylamidophosphoryloxy)-γ-pyrone   Compound 75

3-(O-methyl-N-sec-butylamidophosphoryloxy)-γ-pyrone   Compound 76

3-(O-methyl-N-cyclohexylamidophosphoryloxy)-γ-pyrone   Compound 77

3-(O-methyl-N-phenylamidophosphoryloxy)-γ-pyrone   Compound 78

3-(O-methyl-N-benzylamidophosphoryloxy)-γ-pyrone   Compound 79

3-(O-methyl-N,N-dimethylamidophosphoryloxy)-γ-pyrone   Compound 80

3-(O-methyl-N,N-diethylamidophosphoryloxy)-γ-pyrone   Compound 81

3-(O-methyl-piperidinophosphoryloxy)-γ-pyrone   Compound 82

3-(O-methyl-N-n-propylamidophosphoryloxy)-2-methyl-γ-pyrone   Compound 83

3-(O-methyl-N,N-diethylamidophosphoryloxy)-2-propyl-γ-pyrone   Compound 84

3-(O-ethyl-N-methylamidophosphoryloxy)-γ-pyrone   Compound 85

3-(O-ethyl-N-ethylamidophosphoryloxy)-γ-pyrone   Compound 86

3-(O-ethyl-N-n-propylamidophosphoryloxy)-γ-pyrone   Compound 87

3-(O-ethyl-N-isopropylamidophosphoryloxy)-γ-pyrone   Compound 88

3-(O-ethyl-N-n-butylamidophosphoryloxy)-γ-pyrone   Compound 89

3-(O-ethyl-N-isobutylamidophosphoryloxy)-γ-pyrone   Compound 90

3-(O-ethyl-N-sec-butylamidophosphoryloxy)-γ-pyrone   Compound 91

3-(O-ethyl-N,N-dimethylamidophosphoryloxy)-γ-pyrone   Compound 92

3-(O-ethyl-N,N-diethylamidophosphoryloxy)-γ-pyrone   Compound 93

3-(O-ethyl-N-cyclohexylamidophosphoryloxy)-γ-pyrone   Compound 94

3-(O-ethyl-N,N-dibutylamidophosphoryloxy)-γ-pyrone   Compound 95

3-(O-ethyl-N-phenylamidophosphoryloxy)-γ-pyrone   Compound 96

3-(O-ethyl-N-benzylamidophosphoryloxy)-γ-pyrone    Compound 97
3-(O-ethyl-N-methyl-N-butylamidophosphoryloxy)-γ-pyrone    Compound 98
3-(O-ethyl-N-ethyl-N-butylamidophosphoryloxy)-γ-pyrone    Compound 99
3-(O-ethyl-N-ethylamidophosphoryloxy)-2-ethyl-γ-pyrone    Compound 100
3-(O-ethyl-N-isopropylamidophosphoryloxy)-2-ethyl-γ-pyrone    Compound 101
3-(O-ethyl-N,N-dimethylamidophosphoryloxy)-2-isobutyl-γ-pyrone    Compound 102
3-(O-propyl-N-isopropylamidophosphoryloxy)-γ-pyrone    Compound 103
3-(O-propyl-N-n-propylamidophosphoryloxy)-γ-pyrone    Compound 104
3-(O-propyl-N-allylamidophosphoryloxy)-γ-pyrone    Compound 105
3-(O-propyl-N-sec-butylamidophosphoryloxy)-γ-pyrone    Compound 106
3-(O-propyl-N-isobutylamidophosphoryloxy)-γ-pyrone    Compound 107
3-(O-propyl-N-cyclohexylamidophosphoryloxy)-γ-pyrone    Compound 108
3-(O-propyl-N,N-dimethylamidophosphoryloxy)-γ-pyrone    Compound 109
3-(O-propyl-N,N-diethylamidophosphoryloxy)-γ-pyrone    Compound 110
3-(O-propyl-N-phenylamidophosphoryloxy)-γ-pyrone    Compound 111
3-(O-propyl-N-benzylamidophosphoryloxy)-γ-pyrone    Compound 112
3-(O-propyl-N,N-dibutylamidophosphoryloxy)-γ-pyrone    Compound 113
3-(O-propyl-N-methyl-N-butylamidophosphoryloxy)-γ-pyrone    Compound 114
3-(O-propyl-N-ethyl-N-butylamidophosphoryloxy)-γ-pyrone    Compound 115
3-(O-propyl-piperidinophosphoryloxy)-γ-pyrone    Compound 116
3-(O-propyl-N-isopropylamidophosphoryloxy)-2-cyclohexyl-γ-pyrone    Compound 117
3-(O-propyl-N,N-dimethylamidophosphoryloxy)-2-allyl-γ-pyrone    Compound 118
3-(O-methyl-N-methylamidothiophosphoryloxy)-γ-pyrone    Compound 119
3-(O-methyl-N-ethylamidothiophosphoryloxy)-γ-pyrone    Compound 120
3-(O-methyl-N-n-propylamidothiophosphoryloxy)-γ-pyrone    Compound 121
3-(O-methyl-N-isopropylamidothiophosphoryloxy)-γ-pyrone    Compound 122
3-(O-methyl-N-isobutylamidothiophosphoryloxy)-γ-pyrone    Compound 123
3-(O-methyl-N-sec-butylamidothiophosphoryloxy)-γ-pyrone    Compound 124
3-(O-methyl-N-cyclohexylamidothiophosphoryloxy)-γ-pyrone    Compound 125
3-(O-methyl-N-benzylamidothiophosphoryloxy)-γ-pyrone    Compound 126
3-(O-methyl-N-propylamidothiophosphoryloxy)-2-isopropyl-γ-pyrone    Compound 127
3-(O-methyl-N,N-diethylamidothiophosphoryloxy)-2-methyl-γ-pyrone    Compound 128
3-(O-ethyl-N-ethylamidothiophosphoryloxy)-γ-pyrone    Compound 129
3-(O-ethyl-N-n-propylamidothiophosphoryloxy)-γ-pyrone    Compound 130
3-(O-ethyl-N-allylamidothiophosphoryloxy)-γ-pyrone    Compound 131
3-(O-ethyl-N-cyclopentylamidothiophosphoryloxy)-γ-pyrone    Compound 132
3-(O-ethyl-N-phenylamidothiophosphoryloxy)-γ-pyrone    Compound 133
3-(O-ethyl-N-benzylamidothiophosphoryloxy)-γ-pyrone    Compound 134
3-(O-ethyl-morpholinothiophosphoryloxy)-γ-pyrone    Compound 135
3-(O-ethyl-N,N-diethylamidothiophosphoryloxy)-γ-pyrone    Compound 136
3-(O-ethyl-N-isopropylamidothiophosphoryloxy)-2-methyl-γ-pyrone    Compound 137
3-(O-ethyl-N,N-dimethylamidothiophosphoryloxy)-2-ethyl-γ-pyrone    Compound 138
3-(O-propyl-N-propylamidothiophosphoryloxy)-γ-pyrone    Compound 139
3-(O-propyl-N-cyclohexylamidothiophosphoryloxy)-γ-pyrone    Compound 140
3-(O-propyl-N-benzylamidothiophosphoryloxy)-γ-pyrone    Compound 141
3-(O-propyl-N-benzylamidothiophosphoryloxy)-2-methyl-γ-pyrone    Compound 142
3-(O-propyl-N,N-diethylamidothiophosphoryloxy)-2-cyclohexyl-γ-pyrone    Compound 143

The compounds of the present invention represented by the general formula [I] have excellent insecticidal and miticidal activities. That is, the compounds represented by the general formula [I] exhibit particularly high activity against insect pests and mites and also against sanitary insect pests to health, whereas they are reasonably within the tolerance of plants and are of very low toxicity to warm-blooded animals. As such, the compounds of the invention are effective against pests at all stages or particular stages of its growth and can therefore be effectively used in order to control pests in crop land and forest.

The pests as mentioned above include, for example, those of isoptera, such as Formosan subterranean termite, and Japanese termite; those of thysanoptera, such as rice thrips, and onion thrips; those of orthoptera, such as rice grasshopper, Asiatic locust, field cricket, and American cockroach; those of hemiptera, such as bean aphid, soy bean aphid, cabbage aphid, black rice bug, rice stink bug, green plant bug, comstock mealybug, horned wax scale, small brown planthopper, green rice leafhopper, two-spotted small leafhopper, pear sucker, Japanese pear lace bug, green broad-winged planthopper, wooly apple aphis, brown rice planthopper, white-backed rice planthopper, green peach aphid, and cotton aphid; those of lepidopera, such as small white butterfly, smaller citrus dog, akebia leaf-like moth, oriental moth, fruit-piercing moth, sweetpotato horn worm, nut fruit tortrix, tent caterpillar, Azuki pod worm, fall webworm, long tailed blue, sweet-potato leafworm, oriental tobacco budworm, diamond back moth, rice leaf roller, butterbur webworm, rice stem borer, pink borer, honey moth, cotton bollworm, tobacco budworm, pink bollworm, corn stalk borer, oriental corn borer, and oriental fruit moth; those of coleoptera, such as rice leaf beetle, mulberry borer, Japanese pine engraver, rice weevil, Azuki beam weevil, rice plant weevil, cupreous chafer, broad bean weevil, black maize beetle, rice water weevil, sugarcane wireworm, and cotton boll weevil; those of hymenoptera, such as cabbage sawfly, and soy bean sawfly; those of diptera, such as rice crane fly, rice stem maggot, rice leaf minor, soy bean pod gall midge, Trypetidae, and house fly; mites such as citrus red mite, carmine mite, sweet cherry spider mite, brown mite, bulb mite, Japanese citrus rust mite, two-spotted spider mite, and European red mite; and nematodes such as strawberry bud nematode, southern root-knot nematode, and coffee root leison nematode.

The compounds of the invention show good activities against these pests and may be used in various forms, such as emulsion, wettable powder, suspension, fine particle, dust, water-dispersible powder, coating composition, foam spray formulations aerosol product, microcapsule product, impregnation with a natural or synthetic material, fumigant, and concentrated compound for small-amount spraying. In preparing these formulations, various kinds of surfactants may be used for the purpose of emulsifying dispersing, suspending, or foaming. For example, nonionic surfactants include polyoxyethylene alkyl ether, polyoxyethylene alkyl ester, polyoxyethylene sorbitan alkyl ester, sorbitan alkyl ester, etc.; anionic surfactants include alkylbenzene sulfonate, alkyl sulfosuccinate, alkyl sulfate, polyoxyethylene alkyl sulfate, aryl sulfonate, lignin sulfite, etc. Various organic solvents, aerosol propellants natural minerals and plants, synthetic materials, etc. can be used as a dissolving agent, diluent or carrier. Preferable examples of organic solvents are benzene, toluene, xylene, ethylbenzene, chlorobenzene, alkylnaphthalene, dichloromethane, chloroethylene, cyclohexane, cyclohexanone, acetone, methyl ethyl ketone, methyl isobutyl ketone, alcohols, dimethyl formamide, dimethyl sulfoxide, acetonitrile, mineral oils, etc. Examples of useful aerosol propellants are propane, butane, halogenated hydrocarbon, nitrogen, carbon dioxide, etc. Examples of minerals are kaolin, talc, bentonite, diatomaceous earth, clay, montmorillonite, chalk, calcite, pumice, sepiolite, dolomite, etc. Examples of plants are walnut shell, tabacco stem, sawdust, etc. Examples of synthetic high molecular compounds are alumina, silicate, sugar polymer, etc. Examples of stickers are carboxymethyl cellulose, gum arabic, polyvinyl alcohol, polyvinyl acetate, etc. It is possible to color the preparation with use of organic or inorganic dyes. In the invention, the preparation may contain the present compound in an amount of about 0.1 to 95% by weight, preferably about 0.5 to 90% by weight.

The obtained preparation can be used with or without dilution with a carrier or water. It can be diluted in the range of about 0.00001 to 100% by weight of the effective compound as desired but is preferably diluted in such that it contains the effective compound in an amount of about 0.0001 to 10% by weight. The amount to be applied depends on numbers of noxious insects, weather, etc. but usually about 0.1 to 10 kg, preferably about 0.1 to 1.0 kg of the effective component per one hectare.

The present invention will be described in more detail with reference to examples and test examples.

EXAMPLE 1

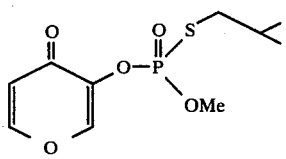

(Compound 3)

To a mixture of 1.12 g of 3-hydroxy-γ-pyrone, 1.1 g of triethylamine and 10 ml of dichloromethane was gradually added dropwise with stirring 2.1 g of O-methyl-S-isobutylthiophosphoric acid chloride, while maintaing the reaction mixture below 10° C. After completion of addition, the mixture was further stirred for about one hour at room temperature. Then, to the reaction mixture were added carbon tetrachloride and water for extraction. The carbon tetrachloride layer was washed with a saturated aqueous solution of sodium chloride and dried on anhydrous magnesium sulfate. By evaporation of the solvent, 2.6 g of 3-(O-methyl, S-isobutylthiophosphoryloxy)-γ-pyrone was obtained as light yellow oil.

$^1$H NMR (CDCl$_3$) δ 8.00 (d, 1H). 7.72 (d, 1H), 6.29 (d, 1H), 3.82 (d, 3H), 3.04–2.62 (m, 2H), 2.14–1.77 (m, 1H), 0.99 (d, 6H)

λmax (neat) 1660 (C=O), 1580 (C=C), 1260 (P=O)cm$^{-1}$

EXAMPLE 2

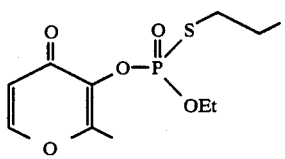

(Compound 35)

To a mixture of 1.26 g of 2-methyl-3-hydroxy-γ-pyrone, 1.2 g of N,N-dimethylaniline and 10 ml of dichloromethane was gradually added dropwise with stirring 2.1 g of O-ethyl-S-n-propylthiophosphoric acid chloride, while maintaing the reaction mixture below 10° C. After completion of addition, the mixture was further stirred for about one hour at room temperature. Then, to the reaction mixture were added carbon tetrachloride and water for extraction. The carbon tetrachloride layer was washed with a saturated aqueous solution of sodium chloride and dried on anhydrous magnesium sulfate. By evaporation of the solvent, 2.7 g of 3-(O-ethyl, S-n-propylthiophosphoryloxy)-2-methyl-γ-pyrone was obtained as light yellow oil.

$^1$H NMR (CDCl$_3$) δ 7.60 (d, 1H), 6.32 (d, 1H), 4.60–4.18 (m, 2H), 3.30–2.75 (m, 2H), 2.42 (d, 3H), 2.00–1.40 (m, 2H), 1.40 (t, 3H), 1.00 (t, 3H)

λmax (neat) 1660 (C=O), 1580 (C=C), 1260 (P=O)cm$^{-1}$

EXAMPLE 3

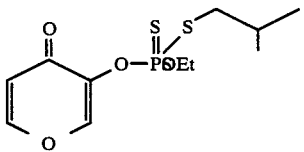

(Compound 59)

To a solution of 1.12 g of 3-hydroxy-γ-pyrone and 20 ml of acetonitrile was added 1.4 g of anhydrous potassium carbonate with stirring. To the mixture was added dropwise 2.2 g of O-ethyl-S-isobutyldithiophosphoric chloride over a period of 10 minutes. After completion of addition, the mixture was reacted with stirring at 50° C. for 5 hours. The reaction mixture was cooled to room temperature and the resulting inorganic salt was filtered. The filtrate was concentrated under a reduced pressure to obtain 2.5 g of 3-(O-ethyl, S-isobutyldithiophosphoryloxy)-γ-pyrone in the form of light yellow oil.

¹H NMR (CDCl₃) δ 8.00 (d, 1H), 7.67 (d, 1H), 6.32 (d, 1H), 4.53–3.96 (m, 2H), 3.15–2.69 (m, 2H), 2.15–1.50 (m, 1H), 1.36 (t, 3H), 0.98 (d, 6H)

λmax (neat) 1660 (C=O), 1580 (C=C), 790 (P=S), 663 (P=S) cm⁻¹

EXAMPLE 4

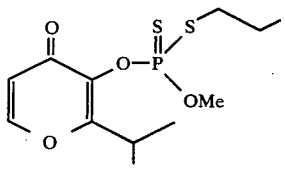

(Compound 66)

To a solution of 1.54 g of 2-isopropyl-3-hydroxy-γ-pyrone and 20 ml of dimethylformamide was added 1.4 g of anhydrous potassium carbonate with stirring. To the mixture was added dropwise 2.1 g of O-methyl-S-n-propyldithiophosphoric chloride over a period of 10 minutes. After completion of addition, the mixture was reacted with stirring at 50° C. for 5 hours. The reaction mixture was cooled to room temperature and the resulting inorganic salt was filtered. To the filtrate were added a saturated aqueous solution of sodium chloride and ethyl acetate for extraction. The ethyl acetate layer was washed with dilute HCl, then with a saturated NaCl solution and dried on anhydrous magnesium sulfate. By evaporation of the solvent, 2.6 g of 3-(O-methyl, S-n-propyldithiophosphoryloxy)-2-isopropyl-γ-pyrone was obtained as light yellow oil.

¹H NMR (CDCl₃) δ 7.67 (d, 1H), 6.28 (d, 1H), 3.70 (d, 3H), 3.75–3.15 (m, 1H), 3.27–2.67 (m, 2H), 2.00–1.22 (m, 2H), 1.23 (d, 6H), 0.97 (t, 3H)

λmax (neat) 1660 (C=O), 1580 (C=C), 790 (P=S), 663 (P=S) cm⁻¹

EXAMPLE 5

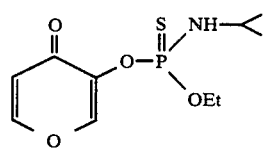

To a dispersion of 7.9 g of 60% sodium hydride and 300 ml of anhydrous tetrahydrofuran was gradually added 20 g of 3-hydroxy-γ-pyrone. To the mixture was added dropwise 39.6 g of O-ethyl-N-isopropylamidothiophosphoryl chloride over a period of 10 minutes. After completion of addition, the mixture was stirred for 3 hours at 50° C. Tetrahydrofuran was removed at a reduced pressure to obtain a residue. The residue was dissolved in chloroform and the solution was washed with 10% aqueous solution of HCl, saturated aqueous solution of NaHCO₃ and then saturated aqueous solution of NaCl. The washed solution was dried on anhydrous magnesium sulfate. By evaporation of chloroform, 49 g of 3-(O-ethyl, N-isopropylamidothiophosphoryloxy)-γ-pyrone was obtained as light yellow oil.

¹H NMR (CCl₄) δ 8.04 (d, 1H), 7.80 (d, 1H), 6.45 (d, 1H), 4.07 (dq, 2H), 4.4–3.8 (m, 1H, NH), 3.8–3.2 (m, 1H), 1.32 (t, 3H), 1.15 (dd, 6H)

λmax (CHCl₃) 3450, 1656, 1633 cm⁻¹

The typical examples of the present compounds are given in Table 1, which are obtained in the same manner as in Examples 1 to 5. In the Table, infrared absorption was shown in IR (neat, cm⁻¹) and nuclear magnetic resonance in NMR (CDCl₃, δ) or (CCl₄, δ).

TABLE 1

| Compn. No. | Compound | State | Spectroscopic data |
|---|---|---|---|
| 1 | (structure) | light yellow oil | ¹HNMR(CCl₄)δ8.01(d,1H), 7.65(d,1H),6.27(d,1H), 3.81(d,3H),3.70(d,3H) λmax(neat)1660(C=O), 1580(C=C),1260(P=O)cm⁻¹ |
| 2 | (structure) | light yellow oil | ¹HNMR(CCl₄)δ8.00(d,1H), 7.68(d,1H),6.27(d,1H), 3.81(d,3H),3.2~2.6(m,2H), 1.9~1.4(m,2H),1.00(t,3H) λmax(neat)1660(C=O), 1580(C=C),1260(P=O)cm⁻¹ |
| 4 | (structure) | light yellow oil | ¹HNMR(CDCl₃)δ8.00(d,1H), 7.65(d,1H),6.27(d,1H), 3.80(d,3H),4.00~3.30(m,1H), 3.2~2.6(m,2H),1.41(d,3H), 1.00(t,3H) λmax(neat)1660(C=O), 1580(C=C),1260(P=O)cm⁻¹ |

TABLE 1-continued

| Compn. No. | Compound | State | Spectroscopic data |
|---|---|---|---|
| 6 | (structure) | light yellow oil | ¹HNMR(CDCl$_3$)δ8.21(d,1H), 7.82(d,1H),6.43(d,1H), 4.6~4.05(m,2H), 3.25~2.70(m,2H), 2.00~1.40(m,2H), 1.40(5,3H),1.00(t,3H) λmax(neat)1660(C=O), 1580(C=C),1260(P=O)cm$^{-1}$ |
| 8 | (structure) | light yellow oil | ¹HNMR(CDCl$_3$)δ8.17(d,1H), 7.78(d,1H),6.44(d,1H), 4.6~4.05(m,2H), 3.15~2.60(m,2H), 2.25~1.55(m,1H), 1.40(t,3H),0.99(d,6H) λmax(neat)1660(C=O) 1580(C=C),1260(P=O)cm$^{-1}$ |
| 11 | (structure) | light yellow oil | ¹HNMR(CDCl$_3$)δ8.00(d,1H), 7.72(d,1H),6.82(d,1H), 4.35~3.89(m,2H), 3.22~2.62(m,2H), 2.00~1.20(m,10H), 0.99(t,6H) λmax(neat)1660(C=O), 1580(C=C),1260(P=O)cm$^{-1}$ |
| 12 | (structure) | light yellow oil | ¹HNMR(CDCl$_3$)δ8.00(d,1H), 7.73(d,1H),6.28(d,1H), 5.15~4.50(m,1H), 3.30~2.65(m,2H), 2.10~1.45(m,2H), 1.40(d,6H),1.02(t,3H) λmax(neat)1660(C=O), 1580(C=C),1260(P=O)cm$^{-1}$ |
| 14 | (structure) | light yellow oil | ¹HNMR(CCl$_4$)δ8.00(d,1H), 7.72(d,1H),6.27(d,1H), 3.90(t,2H),3.05~2.63(m,2H), 2.25~1.55(m,2H), 0.97(d,12H) λmax(neat)1660(C=O), 1580(C=C),1260(P=O)cm$^{-1}$ |
| 5 | (structure) | light yellow oil | ¹HNMR(CDCl$_3$)δ8.00(d,1H), 7.75(d,1H),6.29(d,1H), 3.80(d,3H),3.3~2.5(m,2H), 2.0~1.6(m,1H), 1.8~1.3(m,2H),0.90(d,6H) λmax(neat)1660(C=O), 1580(C=C),1260(P=O)cm$^{-1}$ |
| 21 | (structure) | light yellow oil | ¹HNMR(CDCl$_3$)δ7.85(d,1H), 7.63(d,1H),8.0~7.2(m,5H), 6.40(d,1H),4.6~4.05(m,2H), 1.29(t,3H) λmax(neat)1660(C=O), 1580(C=C),1260(P=O)cm$^{-1}$ |
| 23 | (structure) | light yellow oil | ¹HNMR(CDCl$_3$)δ8.00(d,1H), 7.75(d,1H),6.30(d,1H), 3.81(d,3H),3.25~1.5(m,1H), 2.1~1.4(m,10H) λmax(neat)1660(C=O), 1580(C=C),1260(P=O)cm$^{-1}$ |

TABLE 1-continued

| Compn. No. | Compound | State | Spectroscopic data |
|---|---|---|---|
| 24 | (structure) | light yellow oil | ¹HNMR(CDCl₃)δ8.00(d,1H), 7.72(d,1H),6.28(d,1H), 4.9~4.35(m,1H), 3.05~2.63(m,2H), 2.2~1.6(m,1H), 2.1~1.4(m,10H),0.97(d,6H) λmax(neat)1660(C=O), 1580(C=C),1260(P=O)cm⁻¹ |
| 26 | (structure) | light yellow oil | ¹HNMR(CDCl₃)δ8.18(d,1H), 6.51(s,1H), 4.65~4.05(m,2H),4.35(s,2H), 3.27~2.55(m,2H), 2.10~1.4(m,2H), 1.40(t,3H),1.00(t,3H) λmax(neat)1660(C=O), 1580(C=C),1260(P=O)cm⁻¹ |
| 28 | (structure) | light yellow oil | ¹HNMR(CDCl₃)δ8.04(d,1H), 6.19(s,1H),4.60~4.00(m,2H), 3.30~2.70(m,2H),2.28(s,3H), 2.0~1.4(m,2H),1.40(t,3H), 1.00(t,3H) λmax(neat)1660(C=O), 1580(C=C),1260(P=O)cm⁻¹ |
| 29 | (structure) | light yellow oil | ¹HNMR(CDCl₃)δ8.09(d,1H), 6.23(s,1H),4.6~4.0(m,2H), 3.1~2.7(m,2H),2.29(s,3H), 2.2~1.4(m,1H),1.40(t,3H), 1.00(d,6H) λmax(neat)1660(C=O), 1580(C=C),1260(P=O)cm⁻¹ |
| 32 | (structure) | light yellow oil | ¹HNMR(CDCl₃)δ6.09(s,1H), 4.62~4.07(m,2H), 3.27~2.73(m,2H),2.38(d,3H), 2.24(s,3H),2.08~1.40(m,2H), 1.39(t,3H),1.00(t,3H) λmax(neat)1660(C=O), 1580(C=C),1260(P=O)cm⁻¹ |
| 36 | (structure) | light yellow oil | ¹HNMR(CDCl₃)δ7.69(d,1H), 6.27(d,1H),4.60~4.05(m,2H), 3.25~2.75(m,2H), 2.78(brq,2H), 2.00~1.40(m,2H),1.40(t,3H), 1.24(t,3H),1.00(t,3H) λmax(neat)1660(C=O), 1580(C=C),1260(P=O)cm⁻¹ |
| 33 | (structure) | light yellow oil | ¹HNMR(CDCl₃)δ8.90(d,1H), 6.23(d,1H),3.82(d,3H), 3.1~2.7(m,2H),2.29(s,3H), 2.2~1.4(m,1H),1.00(d,6H) λmax(neat)1660(C=O), 1580(C=C),1260(P=O)cm⁻¹ |
| 40 | (structure) | light yellow oil | ¹HNMR(CDCl₃)δ7.65(d,1H), 6.25(d,1H),3.82(d,3H), 3.75~3.15(m,1H), 3.12~2.70(m,2H), 2.15~1.50(m,1H), 1.25(d,6H),1.00(d,6H) λmax(neat)1660(C=O), 1580(C=C),1260(P=O)cm⁻¹ |

TABLE 1-continued

| Compn. No. | Compound | State | Spectroscopic data |
|---|---|---|---|
| 44 | | light yellow oil | $^1$HNMR(CDCl$_3$)δ7.58(d,1H), 6.24(d,1H),4.60~4.00(m,2H), 3.45~2.85(m,1H), 3.30~2.75(m,2H), 2.00~1.40(m,4H), 1.38(t,3H),1.23(d,3H), 1.00(t,3H),0.89(t,3H) λmax(neat)1660(C=O), 1580(C=C),1260(P=O)cm$^{-1}$ |
| 38 | | light yellow oil | $^1$HNMR(CDCl$_3$)δ7.58(d,1H), 6.24(d,1H),4.57~4.05(m,2H), 3.25~2.75(m,2H), 2.95~2.60(m,2H), 2.00~1.40(m,4H), 1.40(t,3H),1.00(t,3H) λmax(neat)1660(C=O), 1580(C=C),1260(P=O)cm$^{-1}$ |
| 46 | | light yellow oil | $^1$HNMR(CDCl$_3$)δ7.56(d,1H), 6.23(d,1H),4.58~4.00(m,2H), 3.23~2.70(m,2H),2.64(d,2H), 2.3~1.8(m,1H), 2.0~1.4(m,2H),1.39(t,3H), 1.00(t,3H),0.96(d,6H) λmax(neat)1660(C=O), 1580(C=C),1260(P=O)cm$^{-1}$ |
| 48 | | light yellow oil | $^1$HNMR(CCl$_4$)δ7.47(d,1H), 6.11(d,1H),3.80(d,3H), 3.2~2.7(m,2H),2.65(t,2H), 2.15~1.50(m,1H), 1.7~1.2(m,8H), 1.00(d,6H),1.00(t,3H) λmax(neat)1660(C=O), 1580(C=C),1260(P=O)cm$^{-1}$ |
| 50 | | light yellow oil | $^1$HNMR(CDCl$_3$)δ7.61(d,1H), 6.24(d,1H),4.60~4.00(m,2H), 3.4~2.8(brs,1H), 3.30~2.70(m,2H), 2.1~1.4(m,12H), 1.40(t,3H),1.00(t,3H), λmax(neat)1660(C=O), 1580(C=C),1260(P=O)cm$^{-1}$ |
| 53 | | light yellow oil | $^1$HNMR(CDCl$_3$)δ8.0~7.7 (m,2H),7.82(d,1H), 7.7~7.35(m,3H),6.42(d,1H), 4.60~4.00(m,2H), 3.30~2.70(m,2H), 2.0~1.4(m,2H),1.40(t,3H), 1.00(t,3H) λmax(neat)1660(C=O), 1580(C=C),1260(P=O)cm$^{-1}$ |
| 55 | | light yellow oil | $^1$HNMR(CDCl$_3$)δ7.82(d,1H), 6.40(d,1H),5.73(m,1H), 5.29(m,1H),5.09(m,1H), 4.60~4.00(m,2H),3.50(d,2H), 3.30~2.70(m,2H), 2.0~1.4(m,2H),1.40(t,3H), 1.00(t,3H) λmax(neat)1660(C=O), 1580(C=C),1260(P=O)cm$^{-1}$ |
| 58 | | light yellow oil | $^1$HNMR(CDCl$_3$)δ7.90(d,1H), 7.61(d,1H),6.24(d,1H), 4.48~3.92(m,2H), 3.27~2.67(m,2H), 2.00~1.22(m,2H), 1.34(t,3H),0.95(t,3H) λmax(neat)1660(C=O), 1580(C=C),790,663(P=S)cm$^{-1}$ |

| Compn. No. | Compound | State | Spectroscopic data |
|---|---|---|---|
| 64 | (structure: 4H-pyran-4-one with O-P(=S)(OMe)(S-isobutyl) substituent) | light yellow oil | $^1$HNMR(CDCl$_3$)δ8.00(d,1H), 7.67(d,1H),6.28(d,1H), 3.70(d,3H),3.15~2.70(m,2H), 2.20~1.60(m,1H),0.97(d,6H), λmax(neat)1660(C=O), 1580(C=C),790(P=S), 663(P=S)cm$^{-1}$ |
| 68 | (structure: pyranone with O-P(=S)(OMe)(S-isobutyl) and isopropyl substituent) | light yellow oil | $^1$HNMR(CDCl$_3$)δ7.67(d,1H), 6.28(d,1H),3.70(d,3H), 3.75~3.15(m,1H), 3.15~2.70(m,2H), 2.20~1.60(m,1H), 1.23(d,6H),1.00(d,6H) λmax(neat)1660(C=O), 1580(C=C),790(P=S), 663(P=S)cm$^{-1}$ |
| 70 | (structure: pyranone with O-P(=O)(OMe)(NHMe)) | light yellow oil | $^1$HNMR(CDCl$_3$)δ7.98(d,1H), 7.62(d,1H),6.30(d,1H), 3.70(d,3H), 3.70~3.25(m,1H), 2.70(d,3H) λmax(CHCl$_3$)3470,1654, 1632cm$^{-1}$ |
| 73 | (structure: pyranone with O-P(=O)(OMe)(NH-iPr)) | light yellow oil | $^1$HNMR(CDCl$_3$)δ8.00(d,1H), 7.61(d,1H),6.32(d,1H), 3.72(d,3H), 3.70~3.27(m,2H), 1.15(dd,6H) λmax(CHCl$_3$)3470,1655, 1632cm$^{-1}$ |
| 72 | (structure: pyranone with O-P(=O)(OMe)(NH-propyl)) | light yellow oil | $^1$HNMR(CDCl$_3$)δ8.03(d,1H), 7.62(d,1H),6.34(d,1H), 4.05~3.55(m,1H), 3.72(d,3H), 3.15~2.62(m,2H), 1.80~1.18(m,2H), 0.88(t,3H) λmax(CHCl$_3$)3470,1656, 1631cm$^{-1}$ |
| 76 | (structure: pyranone with O-P(=O)(OMe)(NH-sec-butyl)) | light yellow oil | $^1$HNMR(CDCl$_3$)δ8.08(d,1H), 7.69(d,1H),6.36(d,1H), 4.00~3.48(m,1H), 3.72(d,3H), 3.42~2.85(m,1H), 1.60~1.20(m,2H), 1.11(dd,3H),0.86(t,3H) λmax(CHCl$_3$)3470,1655 1632cm$^{-1}$ |
| 75 | (structure: pyranone with O-P(=O)(OMe)(NH-isobutyl)) | light yellow oil | $^1$HNMR(CDCl$_3$)δ8.09(d,1H), 7.72(d,1H),6.37(d,1H), 4.20~3.70(m,1H), 3.72(d,3H), 3.09~2.55(m,2H), 1.90~1.30(m,1H), 0.87(d,6H) λmax(CHCl$_3$)3470,1655, 1632cm$^{-1}$ |
| 79 | (structure: pyranone with O-P(=O)(OMe)(NHCH$_2$Ph)) | light yellow oil | $^1$HNMR(CDCl$_3$)δ7.90(d,1H), 7.53(d,1H),7.08(s,5H), 6.18(d,1H), 5.15~4.65(m,1H), 4.03(dd,2H),3.59(d,3H) λmax(CHCl$_3$)3475,1655, 1631cm$^{-1}$ |

TABLE 1-continued

| Compn. No. | Compound | State | Spectroscopic data |
|---|---|---|---|
| 78 | (structure) | light yellow oil | $^1$HNMR(CDCl$_3$)δ7.95(d,1H), 7.50(d,1H), 7.15~6.75(m,1H), 6.96(s,5H),6.30(d,1H), 3.75(d,3H) λmax(CHCl$_3$)3410,3230, 1652,1628,1602cm$^{-1}$ |
| 83 | (structure) | light yellow oil | $^1$HNMR(CDCl$_3$)δ7.62(d,1H), 6.34(d,1H), 4.10~3.60(m,1H), 3.70(d,3H), 3.15~2.64(m,2H), 2.38(d,3H), 1.80~1.18(m,2H), 0.89(t,3H) λmax(CHCl$_3$)3470,1655, 1631cm$^{-1}$ |
| 80 | (structure) | light yellow oil | $^1$HNMR(CDCl$_3$)δ7.97(d,1H), 7.61(d,1H),6.29(d,1H), 3.69(d,3H),2.69(d,6H) λmax(CHCl$_3$)1657,1631cm$^{-1}$ |
| 81 | (structure) | light yellow oil | $^1$HNMR(CDCl$_3$)δ8.08(d,1H), 7.76(d,1H),6.32(d,1H), 3.70(d,3H), 3.40~2.80(m,4H), 1.08(t,6H) λmax(CHCl$_3$)1656,1632cm$^{-1}$ |
| 82 | (structure) | light yellow oil | $^1$HNMR(CDCl$_3$)δ8.04(d,1H), 7.73(d,1H),6.32(d,1H), 3.71(d,6H), 3.35~2.80(m,4H), 1.53(broad s,6H) λmax(CHCl$_3$)1655,1632cm$^{-1}$ |
| 84 | (structure) | light yellow oil | $^1$HNMR(CDCl$_3$)δ7.76(d,1H), 6.32(d,1H),3.72(d,3H), 3.42~2.80(m,4H), 2.80~2.50(m,2H), 2.05~1.40(m,2H), 1.08(t,6H),1.00(t,3H) λmax(CHCl$_3$)1655,1632cm$^{-1}$ |
| 88 | (structure) | light yellow oil | $^1$HNMR(CCl$_4$)δ8.06(d,1H), 7.69(d,1H),6.30(d,2H), 4.45~4.00(m,1H), 4.30~3.81(m,2H), 3.70~3.15(m,1H), 1.31(t,3H),1.12(d,6H) λmax(CHCl$_3$)3470,1655, 1632cm$^{-1}$ |
| 87 | (structure) | light yellow oil | $^1$HNMR(CDCl$_3$)δ8.08(d,1H), 7.68(d,1H),6.36(d,1H), 4.35~3.88(m,2H), 4.00~3.50(m,1H), 3.20~2.60(m,2H), 1.80~1.25(m,2H), 1.30(t,3H),0.85(t,3H) λmax(CHCl$_3$)3470,1653, 1630cm$^{-1}$ |

TABLE 1-continued

| Compn. No. | Compound | State | Spectroscopic data |
|---|---|---|---|
| 91 | (structure) | light yellow oil | $^1$HNMR(CDCl$_3$)δ8.07(d,1H), 7.72(d,1H),6.33(d,1H), 4.09(dq,2H), 4.07~3.67(m,1H), 3.42~2.87(m,1H), 1.67~1.22(m,2H), 1.32(t,3H),1.12(dd,3H), 0.87(t,3H) λmax(CHCl$_3$)3470,1654, 1634cm$^{-1}$ |
| 90 | (structure) | light yellow oil | $^1$HNMR(CCl$_4$)δ8.06(d,1H), 7.69(d,1H),6.30(d,2H), 4.45~4.00(m,1H), 4.30~3.81(m,2H), 3.70~3.15(m,1H), 1.31(t,3H),1.12(d,6H) λmax(CHCl$_3$)3470,1655, 1632cm$^{-1}$ |
| 97 | (structure) | light yellow oil | $^1$HNMR(CDCl$_3$)δ7.90(d,1H), 7.51(d,1H),6.19(d,1H), 4.06(d,2H), 4.25~3.75(m,2H), 4.30~3.85(m,1H), 1.25(t,3H) λmax(CHCl$_3$)3470,1655, 1632cm$^{-1}$ |
| 96 | (structure) | light yellow oil | $^1$HNMR(CDCl$_3$)δ7.99(d,1H), 7.56(d,1H),7.02(s,5H), 7.15~6.75(m,1H), 6.28(d,1H),4.20(dq,2H), 1.26(t,3H) λmax(CHCl$_3$)3410,3230, 1652,1628,1602cm$^{-1}$ |
| 92 | (structure) | light yellow oil | $^1$HNMR(CDCl$_3$)δ8.00(d,1H), 7.66(d,1H),6.30(d,1H), 4.09(dq,2H),2.69(d,6H), 1.33(t,3H) λmax(CHCl$_3$)1655,1632cm$^{-1}$ |
| 93 | (structure) | light yellow oil | $^1$HNMR(CCl$_4$)δ7.99(d,1H), 7.70(d,1H),6.20(d,1H), 4.02(dq,2H),3.03(dq,4H), 1.31(t,3H),1.03(t,6H) λmax(CHCl$_3$)1657,1632cm$^{-1}$ |
| 95 | (structure) | light yellow oil | $^1$HNMR(CDCl$_3$)δ8.06(d,1H), 7.77(d,1H),6.31(d,1H), 4.07(dq,2H), 3.50~2.70(m,4H), 1.8~1.1(m,8H),1.31(t,3H), 0.88(broad t,6H) λmax(CHCl$_3$)1656,1633cm$^{-1}$ |
| 94 | (structure) | light yellow oil | $^1$HNMR(CDCl$_3$)δ8.01(d,1H), 7.71(d,1H),6.27(d,1H), 4.04(dq,2H), 3.35~2.80(m,4H), 1.50(broad s,6H), 1.32(t,3H) λmax(CHCl$_3$)1654,1631cm$^{-1}$ |

TABLE 1-continued

| Compn. No. | Compound | State | Spectroscopic data |
|---|---|---|---|
| 102 | (structure) | light yellow oil | ¹HNMR(CDCl₃)δ7.60(d,1H), 6.30(d,1H),4.09(dq,2H), 2.69(d,6H), 2.64(broad d,2H), 2.35~1.70(m,1H), 1.33(t,3H),0.97(d,6H) λmax(CHCl₃)1655,1634cm⁻¹ |
| 98 | (structure) | light yellow oil | ¹HNMR(CDCl₃)δ7.96(d,1H), 7.59(d,1H),6.26(d,1H), 4.06(dq,2H), 3.24~2.70(m,2H), 2.66(d,3H), 1.70~1.10(m,4H), 1.32(t,3H), 0.89(broad t,3H) λmax(CHCl₃)1655,1632cm⁻¹ |
| 99 | (structure) | light yellow oil | ¹HNMR(CDCl₃)δ7.93(d,1H), 7.60(d,1H),6.22(d,1H), 4.01(dq,2H), 3.37~2.72(m,4H), 1.7~1.30(m,4H), 1.30(t,3H),1.05(t,3H), 0.87(t,3H) λmax(CHCl₃)1655,1633cm⁻¹ |
| 101 | (structure) | light yellow oil | ¹HNMR(CCl₄)δ7.69(d,1H), 6.30(d,1H) 4.45~4.00(m,1H), 4.30~3.81(m,2H), 3.70~3.15(m,1H), 2.73(q,2H),1.31(t,3H), 1.22(t,3H),1.12(d,6H) λmax(CHCl₃)3470,1654, 1633cm⁻¹ |
| 103 | (structure) | light yellow oil | ¹HNMR(CCl₄)δ8.05(d,1H), 7.72(d,1H),6.27(d,1H), 4.47(broad t,1H), 3.93(q,2H), 3.62~3.02(m,1H), 1.92~1.3(m,2H), 1.10(d,6H),0.92(t,3H) λmax(CHCl₃)3470,1653, 1633cm⁻¹ |
| 104 | (structure) | light yellow oil | ¹HNMR(CCl₄)δ8.06(d,1H), 7.73(d,1H),6.29(d,1H), 4.85~4.20(m,1H), 3.95(q,2H), 3.15~2.55(m,2H), 1.9~1.2(m,4H), 0.95(t,3H),0.86(t,3H) λmax(CHCl₃)3470,1653, 1632cm⁻¹ |
| 105 | (structure) | light yellow oil | ¹HNMR(CDCl₃)δ8.11(d,1H), 7.80(d,1H),6.38(d,1H), 6.12~5.47(m,1H), 5.37~4.82(m,2H), 4.70~4.17(m,1H), 4.02(q,2H), 3.80~3.2(m,2H), 1.97~1.37(m,2H), 0.95(t,3H) λmax(CHCl₃)3470,1655, 1632cm⁻¹ |

TABLE 1-continued

| Compn. No. | Compound | State | Spectroscopic data |
|---|---|---|---|
| 106 | (4-oxo-4H-pyran-3-yl phosphate with sec-butylamino and propoxy) | light yellow oil | ¹HNMR(CDCl₃)δ7.96(d,1H), 7.57(d,1H),6.30(d,1H), 3.97(q,2H), 3.50~2.95(m,2H), 1.95~1.25(m,4H), 1.00(d,3H),0.95(broad t,6H) λmax(CHCl₃)3470,1652, 1630cm⁻¹ |
| 107 | (with isobutylamino and propoxy) | light yellow oil | ¹HNMR(CDCl₃)δ7.98(d,1H), 7.57(d,1H),6.31(d,1H), 3.98(q,2H),4.2~3.8(m,1H), 3.70~3.10(broad s,1H), 2.95~2.55(m,2H), 1.95~1.30(m,2H), 0.92(t,3H),0.86(d,6H) λmax(CHCl₃)3470,1654, 1632cm⁻¹ |
| 108 | (with cyclohexylamino and propoxy) | light yellow oil | ¹HNMR(CDCl₃)δ8.03(d,1H) 7.65(d,1H),6.35(d,1H), 4.00(q,2H), 3.52(broad t,1H), 3.35~2.80(m,1H), 2.0~1.0(m,12H),0.93(t,3H) λmax(CHCl₃)3470,1655, 1632cm⁻¹ |
| 112 | (with benzylamino and propoxy) | light yellow oil | ¹HNMR(CDCl₃)δ7.99(d,1H), 7.59(d,1H),7.18(s,5H), 6.31(d,1H),4.09(d,2H) 3.96(q,2H), 4.29~3.91(m,1H), 1.91~1.41(m,2H), 0.89(t,3H) λmax(CHCl₃)3470,1654, 1631cm⁻¹ |
| 111 | (with phenylamino and propoxy) | light yellow oil | ¹HNMR(CDCl₃)7.93(d,1H), 7.52(d,1H),6.95(s,5H), 7.10~6.60(m,1H), 6.28(d,1H),4.03(q,2H), 1.90~1.40(m,2H), 0.90(t,3H) λmax(CHCl₃)3410,3230, 1652,1628,1602cm⁻¹ |
| 117 | (with isopropylamino, propoxy and cyclohexyl) | light yellow oil | ¹HNMR(CCl₄)δ7.70(d,1H), 6.25(d,1H), 4.47(broad t,1H), 3.93(q,2H), 3.62~2.7(m,2H), 2.0~1.2(m,12H), 1.10(d,6H),0.92(t,3H) λmax(CHCl₃)3470,1654, 1633cm⁻¹ |
| 109 | (with N,N-dimethylamino and propoxy) | light yellow oil | ¹HNMR(CDCl₃)δ8.03(d,1H), 7.76(d,1H),6.32(d,1H), 3.95(q,2H),2.70(d,6H), 2.00~1.40(m,2H), 0.94(t,3H) λmax(CHCl₃)1655,1632cm⁻¹ |
| 110 | (with N,N-diethylamino and propoxy) | light yellow oil | ¹HNMR(CDCl₃)δ8.05(d,1H), 7.62(d,1H),6.29(d,1H), 3.96(q,2H),3.10(dq,4H), 1.93~1.33 (m,2H), 1.06(t,6H),0.95(t,3H) λmax(CHCl₃)1654,1631cm⁻¹ |

TABLE 1-continued

| Compn. No. | Compound | State | Spectroscopic data |
|---|---|---|---|
| 116 | (4-oxo-4H-pyran-3-yl) O-propyl piperidinyl phosphonate | light yellow oil | $^1$HNMR(CDCl$_3$)δ8.05(d,1H), 7.67(d,1H),6.32(d,1H), 3.99(q,2H), 3.35~2.85(m,4H), 1.95~1.35(m,2H), 1.53(broad s,6H), 0.95(t,3H) λmax(CHCl$_3$)1655,1632cm$^{-1}$ |
| 113 | (4-oxo-4H-pyran-3-yl) O-propyl N,N-dipentyl phosphoramidate | light yellow oil | $^1$HNMR(CDCl$_3$)δ8.08(d,1H), 7.70(d,1H),6.32(d,1H), 3.96(q,2H), 3.30~2.68(m,4H), 1.98~1.2(m,10H), 0.95(t,3H),0.90(t,6H) λmax(CHCl$_3$)1655,1633cm$^{-1}$ |
| 118 | (2-allyl-4-oxo-4H-pyran-3-yl) O-propyl N,N-dimethyl phosphoramidate | light yellow oil | $^1$HNMR(CDCl$_3$)δ7.73(d,1H), 6.32(d,1H),6.0~5.5(m,1H), 5.3~4.9(m,2H),3.95(q,2H), 3.5~3.3(m,2H),2.70(d,6H), 2.00~1.40(m,2H), 0.94(t,3H) λmax(CHCl$_3$)1657,1635cm$^{-1}$ |
| 114 | (4-oxo-4H-pyran-3-yl) O-propyl N-methyl-N-butyl phosphoramidate | light yellow oil | $^1$HNMR(CDCl$_3$)δ8.03(d,1H), 7.71(d,1H),6.31(d,1H), 3.96(q,2H), 3.27~2.77(m,2H), 2.68(d,3H), 2.05~1.15(m,6H), 0.96(t,3H),0.88(t,3H) λmax(CHCl$_3$)1655,1633cm$^{-1}$ |
| 115 | (4-oxo-4H-pyran-3-yl) O-propyl N-ethyl-N-butyl phosphoramidate | light yellow oil | $^1$HNMR(CDCl$_3$)δ7.99(d,1H), 7.59(d,1H),6.23(d,1H), 3.92(q,2H), 3.37~2.72(m,4H), 1.87~1.40(m,2H), 1.5~1.1(m,4H), 1.07(t,3H),0.93(t,6H) λmax(CHCl$_3$)1654,1633cm$^{-1}$ |
| 121 | (4-oxo-4H-pyran-3-yl) O-methyl N-propyl phosphoramidothioate | light yellow oil | $^1$HNMR(CDCl$_3$)δ8.00(d,1H), 7.68(d,1H),6.38(d,1H), 4.23~3.72(m,1H), 3.74(d,3H), 3.25~2.62(m,2H), 1.74~1.23(m,2H), 0.99(t,3H), λmax(CHCl$_3$)3450,1656, 1632cm$^{-1}$ |
| 124 | (4-oxo-4H-pyran-3-yl) O-methyl N-sec-butyl phosphoramidothioate | light yellow oil | 1$^1$HNMR(CDCl$_3$)δ8.01(d,1H), 7.68(d,1H),6.37(d,1H), 3.72(d,3H),4.1~3.8(m,1H), 3.59~3.00(m,1H), 1.69~1.14(m,2H), 1.04(d,3H),0.89(t,3H) λmax(CHCl$_3$)3450,1655, 1633cm$^{-1}$ |
| 123 | (4-oxo-4H-pyran-3-yl) O-methyl N-isobutyl phosphoramidothioate | light yellow oil | $^1$HNMR(CDCl$_3$)δ7.97(d,1H), 7.66(d,1H),6.35(d,1H), 4.2~3.7(m,1H),3.68(d,3H), 3.00~2.50(m,2H), 1.92~1.32(m,1H), 0.87(d,6H) λmax(CHCl$_3$)3450,1654 1633cm$^{-1}$ |

TABLE 1-continued

| Compn. No. | Compound | State | Spectroscopic data |
|---|---|---|---|
| 126 | (pyranone-O-P(=S)(OMe)-NHCH2-phenyl) | light yellow oil | ¹HNMR(DMSO-d$_6$+CDCl$_3$)δ 8.95(d,1H),7.79(d,1H), 7.14(s,5H),6.26(d,1H), 6.15~5.7(m,1H), 4.07(dd,2H),3.62(d,3H) λmax(CHCl$_3$)3450,1655, 1632cm$^{-1}$ |
| 125 | (pyranone-O-P(=S)(OMe)-NH-cyclohexyl) | light yellow oil | ¹HNMR(CDCl$_3$)δ9.00(d,1H), 7.65(d,1H),6.36(d,1H), 3.72(d,3H),4.0~3.5(m,1H), 3.5~2.5(m,1H), 2.10~0.85(m,10H) λmax(CHCl$_3$)3450,1655, 1632cm$^{-1}$ |
| 127 | (pyranone-O-P(=S)(OMe)-NH-isobutyl) | light yellow oil | ¹HNMR(CDCl$_3$)δ7.68(d,1H), 6.38(d,1H), 4.23~3.72(m,1H), 3.74(d,3H),3.45(m,1H), 3.25~2.62(m,2H), 1.74~1.23(m,2H), 1.24~(d,6H),0.99(t,3H) λmax(CHCl$_3$)3450,1654, 1633cm$^{-1}$ |
| 128 | (pyranone-O-P(=S)(OMe)-NEt$_2$) | light yellow oil | ¹HNMR(CDCl$_3$)δ7.58(d,1H), 6.26(d,1H),3.74(d,3H), 3.45~2.85(m,4H), 2.36(d,3H),1.06(t,6H) λmax(CHCl$_3$)3450,1656, 1633cm$^{-1}$ |
| 130 | (pyranone-O-P(=S)(OEt)-NH-propyl) | light yellow oil | ¹HNMR(CCl$_4$)δ7.86(d,1H), 7.60(d,1H),6.25(d,1H), 4.02(dq,2H),4.2~3.8(m,1H) 3.20~2.62(m,2H), 1.72~1.35(m,2H), 1.31(t,3H),0.88(t,3H) λmax(CHCl$_3$)3450,1655, 1634cm$^{-1}$ |
| 131 | (pyranone-O-P(=S)(OEt)-NH-allyl) | light yellow oil | ¹HNMR(CDCl$_3$)δ7.97(d,1H), 7.63(d,1H),6.41(d,1H), 6.0~5.4(m,1H), 5.40~4.80(m,2H), 4.07(dq,2H), 3.90~3.38(m,2H), 1.31(t,3H) λmax(CHCl$_3$)3450,1655, 1632cm$^{-1}$ |
| 132 | (pyranone-O-P(=S)(OEt)-NH-cyclopentyl) | light yellow oil | ¹HNMR(CCl$_4$)δ7.94(d,1H), 7.71(d,1H),6.33(d,1H), 4.05(dq,2H), 4.35~3.9(m,1H), 3.9~3.3(m,1H), 1.90~1.35(m,8H), 1.31(t,3H) λmax(CHCl$_3$)3450,1656, 1633cm$^{-1}$ |
| 134 | (pyranone-O-P(=S)(OEt)-NHCH2-phenyl) | light yellow oil | ¹HNMR(CCl$_4$)δ7.80(d,1H), 7.50(d,1H),7.06(s,5H), 6.20(d,1H), 4.65~4.15(m,1H), 4.15(d,2H),3.99(dq,2H), 1.25(t,3H) λmax(CHCl$_3$)3450,1656, 1632cm$^{-1}$ |

TABLE 1-continued

| Compn. No. | Compound | State | Spectroscopic data |
|---|---|---|---|
| 135 | (morpholine derivative) | light yellow oil | ¹HNMR(CCl₄)δ7.92(d,1H), 7.66(d,1H),6.24(d,1H), 4.02(dq,2H), 3.72~3.0(m,8H), 1.31(t,3H) λmax(CHCl₃)1655,1634cm⁻¹ |
| 136 | (N,N-diethyl derivative) | light yellow oil | ¹HNMR(CCl₄)δ7.98(d,1H), 7.58(d,1H),6.26(d,1H), 3.98(dq,2H), 3.45~2.80(m,4H), 1.30(t,3H),1.06(t,6H) λmax(CHCl₃)1655,1632cm⁻¹ |
| 138 | (N,N-dimethyl, ethyl derivative) | light yellow oil | ¹HNMR(CCl₄)δ7.58(d,1H), 6.26(d,1H),3.99(dq,2H), 2.73(q,2H),2.65(d,6H), 1.30(t,3H),1.22(t,3H), λmax(CHCl₃)1656,1633cm⁻¹ |
| 137 | (NH-isopropyl, methyl derivative) | light yellow oil | ¹HNMR(CCl₄)δ7.80(d,1H), 6.45(d,1H),4.05(dq,2H), 4.4~3.8(m,1H), 3.8~3.2(m,1H),2.36(d,3H), 1.32(t,3H),1.16(dd,6H) λmax(CHCl₃)3450,1655, 1632cm⁻¹ |
| 139 | (NH-propyl derivative) | light yellow oil | ¹HNMR(CCl₄)δ8.01(d,1H), 7.80(d,1H),6.40(d,1H), 4.60~4.05(m,1H), 3.95(dt,2H), 3.30~2.65(m,2H), 2.0~1.15(m,4H), 0.94(t,3H),0.87(t,3H) λmax(CHCl₃)3450,1655, 1632cm⁻¹ |
| 140 | (NH-cyclohexyl derivative) | light yellow oil | ¹HNMR(CDCl₃)δ8.03(d,1H), 7.71(d,1H),6.36(d,1H), 3.98(dt,2H),4.1~3.7(m,1H), 3.6~2.8(m,1H), 2.1~1.0(m,10H),0.95(t,3H) λmax(CHCl₃)3450,1655, 1632cm⁻¹ |
| 141 | (NHCH₂-phenyl derivative) | light yellow oil | ¹HNMR(CDCl₃)δ7.87(d,1H), 7.53(d,1H),7.13(s,5H), 6.23(d,1H), 4.65~4.0(m,1H), 4.20(d,2H),3.93(dt,2H), 1.91~1.32(m,2H), 0.86(t,3H) λmax(CHCl₃)3450,1657, 1634cm⁻¹ |
| 142 | (NHCH₂-phenyl, methyl derivative) | light yellow oil | ¹HNMR(CDCl₃)δ7.50(d,1H), 7.13(s,5H),6.20(d,1H), 4.7~4.2(m,1H),4.20(d,2H), 3.91(dt,2H),2.35(d,3H), 1.9~1.35(m,2H), 0.86(t,3H), λmax(CHCl₃)3450,1655, 1633cm⁻¹ |

TABLE 1-continued

| Compn. No. | Compound | State | Spectroscopic data |
|---|---|---|---|
| 143 | (structure: pyranone with O-P(=S)(O-propyl)(N(Et)-Et) and cyclohexyl substituent) | light yellow oil | $^1$HNMR(CCl$_4$)δ7.74(d,1H), 6.36(d,1H),3.96(dt,2H), 3.50~2.70(m,5H), 2.0~1.2(m,12H), 1.06(t,6H),0.95(t,3H) λmax(CHCl$_3$)1656,1632cm$^{-1}$ |

The compound obtained in example is tested for insecticial and miticidal activities. The results are shown below.

TEST EXAMPLE 1

(against tobacco cutworms)

Two parts by weight of sample compound were dissolved in 98 parts by weight of acetone. The solution was diluted to a specified concentration with an aqueous solution of 0.04% of a spreading agent ("Shin Rinoh", Nihon Nohyaku Co., Ltd.). The liquid pesticide thus prepared was sprayed over cabbage leaves until drops thereof fell from the leaves and, after the leaves were allowed to dry in air, 3rd-instar larvae of tobacco cutworm were inoculated upon the leaves; and their mortality after lapse of two days was calculated. The results are shown in Table 2, wherein:

$$\text{Mortality (\%)} = \frac{\text{No. of larvae killed}}{\text{Total no. of larvae sampled}} \times 100$$

TABLE 2

| Compound No. | Concn. of compound (%) | Mortality (%) | Concn. of compound (%) | Mortality (%) |
|---|---|---|---|---|
| 1 | 0.03 | 100 | 0.01 | 100 |
| 2 | 0.03 | 100 | 0.01 | 100 |
| 3 | 0.03 | 100 | 0.01 | 95 |
| 4 | 0.03 | 100 | 0.01 | 85 |
| 5 | 0.03 | 100 | 0.01 | 80 |
| 6 | 0.03 | 100 | 0.01 | 100 |
| 11 | 0.03 | 100 | 0.01 | 80 |
| 12 | 0.03 | 100 | 0.01 | 85 |
| 26 | 0.03 | 100 | 0.01 | 90 |
| 28 | 0.03 | 100 | 0.01 | 100 |
| 32 | 0.03 | 100 | 0.01 | 80 |
| 33 | 0.03 | 100 | 0.01 | 80 |
| 36 | 0.03 | 100 | 0.01 | 90 |
| 40 | 0.03 | 100 | 0.01 | 100 |
| 44 | 0.03 | 100 | 0.01 | 70 |
| 46 | 0.03 | 100 | 0.01 | 80 |
| 50 | 0.03 | 100 | 0.01 | 70 |
| 58 | 0.03 | 100 | 0.01 | 100 |
| 64 | 0.03 | 100 | 0.01 | 90 |
| 68 | 0.03 | 100 | 0.01 | 100 |
| 70 | 0.03 | 90 | 0.01 | 75 |
| 72 | 0.03 | 85 | 0.01 | 70 |
| 75 | 0.03 | 90 | 0.01 | 80 |
| 76 | 0.03 | 90 | 0.01 | 70 |
| 80 | 0.03 | 95 | 0.01 | 80 |
| 83 | 0.03 | 85 | 0.01 | 70 |
| 87 | 0.03 | 90 | 0.01 | 70 |
| 88 | 0.03 | 90 | 0.01 | 75 |
| 90 | 0.03 | 85 | 0.01 | 70 |
| 93 | 0.03 | 85 | 0.01 | 70 |
| 103 | 0.03 | 90 | 0.01 | 80 |
| 106 | 0.03 | 85 | 0.01 | 65 |

TABLE 2-continued

| Compound No. | Concn. of compound (%) | Mortality (%) | Concn. of compound (%) | Mortality (%) |
|---|---|---|---|---|
| 121 | 0.03 | 100 | 0.01 | 100 |
| 122 | 0.03 | 100 | 0.01 | 100 |
| 123 | 0.03 | 100 | 0.01 | 95 |
| 124 | 0.03 | 100 | 0.01 | 100 |
| 127 | 0.03 | 100 | 0.01 | 90 |
| 128 | 0.03 | 95 | 0.01 | 80 |
| 130 | 0.03 | 100 | 0.01 | 95 |
| 131 | 0.03 | 100 | 0.01 | 90 |
| 135 | 0.03 | 85 | 0.01 | 70 |
| 136 | 0.03 | 95 | 0.01 | 70 |
| 137 | 0.03 | 100 | 0.01 | 100 |
| 138 | 0.03 | 100 | 0.01 | 95 |
| 139 | 0.03 | 100 | 0.01 | 95 |
| (A) | 0.03 | 85 | 0.01 | 10 |

[As the control compound (A) was used Ortran (trade mark)]

TEST EXAMPLE 2

(against diamond back moth)

Cabbage plants (at 2- or 3-leave stage) were set in three vinyl pots each having a diameter of 8 cm, and 10 heads of 3rd-instar larvae of diamond back moth were allowed to stay in each pot. A 10 ml/3 pots of sample liquid, prepared to a specified concentration, was sprayed over the leaves; and 24 hours later, the number of survivals was counted to calculate the mortality. The results are shown in Table 3.

It is noted that the sample liquid herein refers to a solution prepared by dissolving 2 parts by weight of sample compound in 98 parts by weight of acetone, the solution being diluted with an aqueous solution of 0.04% of a spreading agent ("Shin Rinoh", Nihon Nohyaku Co., Ltd.).

TABLE 3

| Compound No. | Concn. of compound (%) | Mortality (%) | Concn. of compound (%) | Mortality (%) |
|---|---|---|---|---|
| 1 | 0.04 | 100 | 0.01 | 90 |
| 2 | 0.04 | 95 | 0.01 | 60 |
| 3 | 0.04 | 100 | 0.01 | 100 |
| 4 | 0.04 | 95 | 0.01 | 80 |
| 5 | 0.04 | 90 | 0.01 | 70 |
| 8 | 0.04 | 80 | 0.01 | 50 |
| 23 | 0.04 | 90 | 0.01 | 70 |
| 26 | 0.04 | 80 | 0.01 | 60 |
| 28 | 0.04 | 85 | 0.01 | 70 |
| 33 | 0.04 | 100 | 0.01 | 95 |
| 35 | 0.04 | 90 | 0.01 | 70 |
| 40 | 0.04 | 100 | 0.01 | 90 |
| 44 | 0.04 | 80 | 0.01 | 60 |
| 50 | 0.04 | 80 | 0.01 | 65 |
| 55 | 0.04 | 90 | 0.01 | 70 |
| 58 | 0.04 | 90 | 0.01 | 75 |
| 59 | 0.04 | 80 | 0.01 | 60 |

TABLE 3-continued

| Compound No. | Concn. of compound (%) | Mortality (%) | Concn. of compound (%) | Mortality (%) |
| --- | --- | --- | --- | --- |
| 64 | 0.04 | 100 | 0.01 | 80 |
| 66 | 0.04 | 95 | 0.01 | 70 |
| 68 | 0.04 | 100 | 0.01 | 85 |
| 70 | 0.04 | 80 | 0.01 | 60 |
| 72 | 0.04 | 85 | 0.01 | 60 |
| 75 | 0.04 | 75 | 0.01 | 60 |
| 76 | 0.04 | 80 | 0.01 | 60 |
| 80 | 0.04 | 80 | 0.01 | 60 |
| 81 | 0.04 | 75 | 0.01 | 55 |
| 83 | 0.04 | 85 | 0.01 | 70 |
| 90 | 0.04 | 80 | 0.01 | 60 |
| 93 | 0.04 | 80 | 0.01 | 60 |
| 103 | 0.04 | 75 | 0.01 | 50 |
| 106 | 0.04 | 80 | 0.01 | 60 |
| 121 | 0.04 | 100 | 0.01 | 100 |
| 122 | 0.04 | 100 | 0.01 | 100 |
| 123 | 0.04 | 100 | 0.01 | 95 |
| 124 | 0.04 | 90 | 0.01 | 80 |
| 127 | 0.04 | 95 | 0.01 | 80 |
| 128 | 0.04 | 85 | 0.01 | 70 |
| 130 | 0.04 | 90 | 0.01 | 75 |
| 131 | 0.04 | 85 | 0.01 | 70 |
| 135 | 0.04 | 100 | 0.01 | 95 |
| 136 | 0.04 | 95 | 0.01 | 80 |
| 137 | 0.04 | 90 | 0.01 | 75 |
| 138 | 0.04 | 85 | 0.01 | 60 |
| 139 | 0.04 | 90 | 0.01 | 75 |
| (B) | 0.04 | 80 | 0.01 | 35 |

[As the control compound (B) was used Tokuthion (trade mark)]

TEST EXAMPLE 3

(against *Myzus persicae*)

Ten heads/pot of imagines of *Myzus persicae* were allowed to stay on leaves of cabbage plants set in vinyl pots in a forcing culture house. A 10 ml/3 pots of sample liquid, prepared to a specified concentration, was sprayed over the leaves; and 24 hours later, the number of survivals was counted to calculate the mortality. The results are shown in Table 4.

TABLE 4

| Compound No. | Concn. of compound (%) | Mortality (%) | Concn. of compound (%) | Mortality (%) |
| --- | --- | --- | --- | --- |
| 1 | 0.02 | 100 | 0.005 | 80 |
| 2 | 0.02 | 100 | 0.005 | 85 |
| 3 | 0.02 | 100 | 0.005 | 100 |
| 4 | 0.02 | 100 | 0.005 | 100 |
| 5 | 0.02 | 100 | 0.005 | 70 |
| 8 | 0.02 | 100 | 0.005 | 90 |
| 12 | 0.02 | 100 | 0.005 | 60 |
| 14 | 0.02 | 100 | 0.005 | 95 |
| 21 | 0.02 | 100 | 0.005 | 50 |
| 23 | 0.02 | 100 | 0.005 | 65 |
| 24 | 0.02 | 100 | 0.005 | 80 |
| 26 | 0.02 | 100 | 0.005 | 70 |
| 28 | 0.02 | 100 | 0.005 | 60 |
| 29 | 0.02 | 100 | 0.005 | 75 |
| 33 | 0.02 | 100 | 0.005 | 80 |
| 40 | 0.02 | 100 | 0.005 | 90 |
| 48 | 0.02 | 100 | 0.005 | 75 |
| 64 | 0.02 | 100 | 0.005 | 95 |
| 66 | 0.02 | 100 | 0.005 | 80 |
| 68 | 0.02 | 100 | 0.005 | 85 |
| 70 | 0.02 | 95 | 0.005 | 80 |
| 71 | 0.02 | 90 | 0.005 | 80 |
| 72 | 0.02 | 90 | 0.005 | 80 |
| 75 | 0.02 | 95 | 0.005 | 85 |
| 76 | 0.02 | 95 | 0.005 | 85 |
| 80 | 0.02 | 95 | 0.005 | 80 |
| 81 | 0.02 | 90 | 0.005 | 75 |
| 90 | 0.02 | 95 | 0.005 | 80 |
| 94 | 0.02 | 90 | 0.005 | 80 |
| 105 | 0.02 | 85 | 0.005 | 75 |
| 106 | 0.02 | 90 | 0.005 | 80 |
| 121 | 0.02 | 100 | 0.005 | 100 |
| 122 | 0.02 | 100 | 0.005 | 100 |
| 123 | 0.02 | 100 | 0.005 | 100 |
| 124 | 0.02 | 100 | 0.005 | 100 |
| 126 | 0.02 | 100 | 0.005 | 95 |
| 128 | 0.02 | 100 | 0.005 | 95 |
| 130 | 0.02 | 100 | 0.005 | 90 |
| 131 | 0.02 | 100 | 0.005 | 100 |
| 132 | 0.02 | 95 | 0.005 | 80 |
| 135 | 0.02 | 100 | 0.005 | 95 |
| 136 | 0.02 | 100 | 0.005 | 95 |
| 137 | 0.02 | 100 | 0.005 | 90 |
| 138 | 0.02 | 95 | 0.005 | 80 |
| 139 | 0.02 | 95 | 0.005 | 80 |
| (C) | 0.02 | 100 | 0.005 | 5 |

[As the control compound (C) was used Ortran (trade mark)]

TEST EXAMPLE 4

(against *Tetranychus urticae*)

Two parts by weight of sample compound were dissolved in 98 parts by weight of acetone. The solution was diluted to a specified concentration with an aqueous solution of 0.04% of a spreading agent ("Shin Rinoh", Nihon Nohyaku Co., Ltd.), a liquid miticide being thus prepared. Imagines of *Tetrachychus urticae* were inoculated upon kidney bean plants set in pots, and then the miticide prepared as above was sprayed over the plants until drops thereof fell. The mortality three days later was measured. The results are shown in Table 5.

TABLE 5

| Compound No. | Concn. of compound (%) | Mortality (%) |
| --- | --- | --- |
| 5 | 0.04 | 100 |
|  | 0.005 | 100 |
| 12 | 0.04 | 100 |
|  | 0.005 | 95 |
| 14 | 0.04 | 100 |
|  | 0.005 | 90 |
| 19 | 0.04 | 100 |
|  | 0.005 | 85 |
| 23 | 0.04 | 100 |
|  | 0.005 | 80 |
| 26 | 0.04 | 100 |
|  | 0.005 | 70 |
| 38 | 0.04 | 100 |
|  | 0.005 | 100 |
| 48 | 0.04 | 100 |
|  | 0.005 | 95 |
| 50 | 0.04 | 100 |
|  | 0.005 | 100 |
| 55 | 0.04 | 100 |
|  | 0.005 | 100 |
| 70 | 0.04 | 100 |
|  | 0.005 | 80 |
| 75 | 0.04 | 100 |
|  | 0.005 | 95 |
| 82 | 0.04 | 100 |
|  | 0.005 | 90 |
| 103 | 0.04 | 100 |
|  | 0.005 | 85 |
| 106 | 0.04 | 100 |
|  | 0.005 | 90 |
| 121 | 0.04 | 100 |
|  | 0.005 | 100 |
| 122 | 0.04 | 100 |
|  | 0.005 | 100 |
| 123 | 0.04 | 100 |
|  | 0.005 | 100 |

TABLE 5-continued

| Compound No. | Concn. of compound (%) | Mortality (%) |
| --- | --- | --- |
| 132 | 0.04 | 100 |
|  | 0.005 | 95 |
| 137 | 0.04 | 100 |
|  | 0.005 | 90 |
| (D) | 0.04 | 100 |
|  | 0.005 | 70 |

(As the control compound (D) was used Kelthane.)

We claim:

1. γ-Pyrone phosphoric ester derivative represented by the general formula

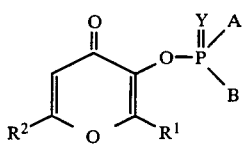

[I]

wherein $R^1$ is hydrogen, lower alkyl group, lower alkenyl group, cycloalkyl group or phenyl group, $R^2$ is hydrogen or lower alkyl group unsubstituted or substituted with halogen atom, A is $-SR^3$ or $-NR^4R^5$, B is $OR^6$, $R^3$ being lower alkyl group, cycloalkyl group or phenyl group, $R^4$ being hydrogen or lower alkyl group, $R^5$ being lower alkyl group, lower alkenyl group, cycloalkyl group, phenyl group or benzyl group, $R^4$ and $R^5$ may link to form piperidino or morpholino group, $R^6$ being lower alkyl group, cycloalkyl group or phenyl group, Y is oxygen or sulfur atom.

2. An insecticidal or miticidal composition comprising, as an effective component for agricultural and horticultural uses, γ-pyrone phosphoric ester derivative as claimed in claim 1, in association with an acceptable carrier or diluent.

3. A composition according to claim 2, in which said ester derivative is present in an amount of about 0.1 to 95% by weight.

4. A composition according to claim 3, wherein said amount is about 0.5 to 90% by weight.

5. A composition according to claim 2, wherein said ester derivative is present in an amount of about 0.0001 to 10% by weight.

* * * * *